(12) United States Patent
Burkholz et al.

(10) Patent No.: US 9,352,119 B2
(45) Date of Patent: May 31, 2016

(54) BLOOD CONTROL IV CATHETER WITH ANTIMICROBIAL PROPERTIES

(75) Inventors: Jonathan Karl Burkholz, Salt Lake City, UT (US); S. Ray Isaacson, Roy, UT (US); Marty L. Stout, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 675 days.

(21) Appl. No.: 13/471,716

(22) Filed: May 15, 2012

(65) Prior Publication Data

US 2013/0310764 A1    Nov. 21, 2013

(51) Int. Cl.
| | |
|---|---|
| A61M 5/00 | (2006.01) |
| A61M 25/00 | (2006.01) |
| A61M 25/06 | (2006.01) |
| A61M 39/06 | (2006.01) |
| A61M 39/02 | (2006.01) |
| A61M 39/26 | (2006.01) |

(52) U.S. Cl.
CPC ....... *A61M 25/0045* (2013.01); *A61M 25/0097* (2013.01); *A61M 25/0606* (2013.01); *A61M 39/0693* (2013.01); *A61M 39/02* (2013.01); *A61M 39/26* (2013.01); *A61M 2025/0056* (2013.01); *A61M 2039/268* (2013.01); *A61M 2205/0238* (2013.01)

(58) Field of Classification Search
CPC .......... A61M 5/24; A61M 2005/3104; A61M 39/045; A61M 39/20; A61M 25/0606; A61M 25/0662; A61B 17/3421; A61L 29/085
USPC .......... 604/167.01–167.04, 167.06, 199, 201, 604/246, 256, 265

See application file for complete search history.

(56) References Cited

U.S. PATENT DOCUMENTS

| | | | |
|---|---|---|---|
| 3,223,629 | A | 12/1965 | Loeffler |
| 3,986,508 | A | 10/1976 | Barrington |
| 4,339,336 | A | 7/1982 | Hammond et al. |
| 4,512,766 | A | 4/1985 | Vailaincourt |

(Continued)

FOREIGN PATENT DOCUMENTS

| | | |
|---|---|---|
| CA | 1331333 | 8/1994 |
| CN | 1526771 A | 9/2004 |

(Continued)

OTHER PUBLICATIONS

"ComfortCoat Hydrophilic Coating," DSM in Medical, http://www.dsm.com/en_US/medical/public/home/pages/product-coating-comfortcoat.jsp, Updated Jan. 11, 2013, Printed Apr. 22, 2013.

(Continued)

*Primary Examiner* — Theodore Stigell
*Assistant Examiner* — Tiffany Legette
(74) *Attorney, Agent, or Firm* — Jeanne Lukasavage; Craig Metcalf; Kirton McConkie

(57) ABSTRACT

A system and method is provided for applying an anti-pathogenic material to various surfaces of a medical device, wherein the method includes identifying various surfaces of the medical tests which include noncritical dimensions, and limiting the application of the anti-pathogenic material to those surfaces. Some aspects of the invention further include the application of an anti-pathogenic lubricant material to various parts or components of a medical device to reduce friction.

10 Claims, 4 Drawing Sheets

(56) References Cited

U.S. PATENT DOCUMENTS

| | | |
|---|---|---|
| 4,584,192 A | 4/1986 | Dell et al. |
| 4,592,920 A | 6/1986 | Murtfeldt |
| 4,629,743 A | 12/1986 | Hong |
| 4,629,746 A | 12/1986 | Michl et al. |
| 4,642,126 A | 2/1987 | Zador et al. |
| 4,677,143 A | 6/1987 | Laurin et al. |
| 4,716,032 A | 12/1987 | Westfall et al. |
| 4,897,427 A | 1/1990 | Barnavon et al. |
| 4,915,934 A | 4/1990 | Tomlinson |
| 4,925,668 A | 5/1990 | Khan et al. |
| 4,933,178 A | 6/1990 | Capelli |
| 5,019,096 A | 5/1991 | Fox, Jr. et al. |
| 5,023,082 A | 6/1991 | Friedman et al. |
| 5,077,352 A | 12/1991 | Elton |
| 5,357,636 A | 10/1994 | Dresdner, Jr. et al. |
| 5,512,199 A | 4/1996 | Khan et al. |
| 5,547,662 A | 8/1996 | Khan et al. |
| 5,616,338 A | 4/1997 | Fox, Jr. et al. |
| 5,629,006 A | 5/1997 | Hoang et al. |
| 5,653,695 A | 8/1997 | Hopkins et al. |
| 5,698,229 A | 12/1997 | Ohsumi et al. |
| 5,773,487 A | 6/1998 | Sokol |
| 5,861,440 A | 1/1999 | Gohla et al. |
| 6,046,143 A | 4/2000 | Khan et al. |
| 6,051,609 A | 4/2000 | Yu et al. |
| 6,127,320 A | 10/2000 | van Ooij et al. |
| 6,242,526 B1 | 6/2001 | Siddiqui et al. |
| 6,248,811 B1 | 6/2001 | Ottersbach et al. |
| 6,326,417 B1 | 12/2001 | Jia |
| 6,337,357 B1 | 1/2002 | Fukunishi et al. |
| 6,344,218 B1 | 2/2002 | Dodd et al. |
| 6,353,041 B1 | 3/2002 | Qian |
| 6,413,539 B1 | 7/2002 | Shalaby |
| 6,488,942 B1 | 12/2002 | Ingemann |
| 6,492,445 B2 | 12/2002 | Siddiqui et al. |
| 6,544,214 B1 | 4/2003 | Utterberg |
| 6,576,633 B1 | 6/2003 | Young et al. |
| 6,861,060 B1 | 3/2005 | Luriya et al. |
| 6,896,889 B2 | 5/2005 | Chevalier et al. |
| 7,074,839 B2 | 7/2006 | Fansler et al. |
| 7,098,256 B2 | 8/2006 | Ong et al. |
| 7,179,849 B2 | 2/2007 | Terry |
| 7,198,800 B1 | 4/2007 | Ko |
| 7,232,540 B2 | 6/2007 | Gould et al. |
| 7,261,925 B2 | 8/2007 | Nesbitt |
| 7,407,707 B2 | 8/2008 | Gould et al. |
| 7,462,401 B2 | 12/2008 | Halfyard et al. |
| 7,494,339 B2 | 2/2009 | Dias et al. |
| 7,498,367 B2 | 3/2009 | Qian |
| 7,514,477 B2 | 4/2009 | Klare et al. |
| 7,704,935 B1 | 4/2010 | Davis et al. |
| 7,816,434 B2 | 10/2010 | Hackbarth et al. |
| 7,871,649 B2 | 1/2011 | Modak et al. |
| 8,034,454 B2 | 10/2011 | Terry |
| 8,034,455 B2 | 10/2011 | Wang et al. |
| 8,067,402 B2 | 11/2011 | Whiteford et al. |
| 8,227,050 B1 | 7/2012 | O'Neil |
| 8,263,102 B2 | 9/2012 | Labrecque et al. |
| 8,268,381 B2 | 9/2012 | Whiteford et al. |
| 8,343,523 B2 | 1/2013 | Toreki et al. |
| 8,343,525 B2 | 1/2013 | Davis et al. |
| 8,388,583 B2 | 3/2013 | Stout et al. |
| 8,840,927 B2 | 9/2014 | DiTizio et al. |
| 2001/0016589 A1 | 8/2001 | Modak et al. |
| 2001/0018095 A1 | 8/2001 | Shlenker et al. |
| 2001/0053895 A1 | 12/2001 | Vaillancourt |
| 2001/0056133 A1 | 12/2001 | Montgomery et al. |
| 2002/0022660 A1 | 2/2002 | Jampani et al. |
| 2002/0028751 A1 | 3/2002 | Lokkesmoe et al. |
| 2002/0040092 A1 | 4/2002 | Siddiqui et al. |
| 2002/0119111 A1 | 8/2002 | Kilgour et al. |
| 2002/0144705 A1 | 10/2002 | Brattesani et al. |
| 2003/0072781 A1 | 4/2003 | Pelerin |
| 2003/0119932 A1 | 6/2003 | Al-Akhdar et al. |
| 2003/0147932 A1 | 8/2003 | Nun et al. |
| 2003/0162839 A1 | 8/2003 | Symington et al. |
| 2003/0170308 A1 | 9/2003 | Cleary et al. |
| 2004/0014864 A1 | 1/2004 | Milic et al. |
| 2004/0039349 A1 | 2/2004 | Modak et al. |
| 2004/0058829 A1 | 3/2004 | Hei et al. |
| 2004/0115477 A1 | 6/2004 | Nesbitt |
| 2004/0185296 A1 | 9/2004 | Mazzanti |
| 2004/0234475 A1 | 11/2004 | Lannibois-Drean et al. |
| 2005/0048005 A1 | 3/2005 | Stockel |
| 2005/0080158 A1 | 4/2005 | Ong et al. |
| 2005/0100580 A1 | 5/2005 | Osborne et al. |
| 2005/0176905 A1 | 8/2005 | Moon et al. |
| 2005/0265931 A1 | 12/2005 | Qian |
| 2006/0051385 A1 | 3/2006 | Scholz |
| 2006/0165751 A1 | 7/2006 | Chudzik et al. |
| 2006/0165903 A1 | 7/2006 | Mazzanti |
| 2006/0239954 A1 | 10/2006 | Sancho |
| 2006/0258780 A1 | 11/2006 | Chaussade et al. |
| 2006/0281663 A1 | 12/2006 | Asmus |
| 2007/0000407 A1 | 1/2007 | Leong |
| 2007/0112112 A1 | 5/2007 | Kerschner et al. |
| 2007/0112146 A1 | 5/2007 | Falk et al. |
| 2007/0141524 A1 | 6/2007 | Brennan et al. |
| 2007/0160547 A1 | 7/2007 | Duffy et al. |
| 2007/0166344 A1 | 7/2007 | Qu et al. |
| 2007/0202177 A1 | 8/2007 | Hoang |
| 2007/0203574 A1 | 8/2007 | McGrath et al. |
| 2007/0225179 A1 | 9/2007 | Schutz et al. |
| 2007/0275101 A1 | 11/2007 | Lu et al. |
| 2008/0026026 A1* | 1/2008 | Lu et al. ................. 424/405 |
| 2008/0075761 A1 | 3/2008 | Modak et al. |
| 2008/0161763 A1 | 7/2008 | Harding et al. |
| 2008/0182921 A1 | 7/2008 | Suh et al. |
| 2009/0110844 A1 | 4/2009 | Platzer et al. |
| 2009/0114327 A1 | 5/2009 | Breunig |
| 2009/0117164 A1 | 5/2009 | Toreki et al. |
| 2009/0162530 A1 | 6/2009 | Nesbitt |
| 2009/0176907 A1 | 7/2009 | Subramanian et al. |
| 2009/0188559 A1 | 7/2009 | Nesbitt |
| 2009/0220739 A1 | 9/2009 | Chougule |
| 2009/0226541 A1 | 9/2009 | Scholz et al. |
| 2009/0317435 A1 | 12/2009 | Vandesteeg et al. |
| 2009/0324666 A1 | 12/2009 | Krongauz et al. |
| 2010/0135949 A1* | 6/2010 | Ou-Yang ................ 424/78.17 |
| 2010/0136209 A1 | 6/2010 | Ou-Yang et al. |
| 2010/0137379 A1* | 6/2010 | Ou-Yang ................. 514/358 |
| 2010/0137472 A1 | 6/2010 | Ou-Yang |
| 2010/0204648 A1* | 8/2010 | Stout et al. ............... 604/122 |
| 2011/0009831 A1* | 1/2011 | Burkholz et al. .......... 604/265 |
| 2011/0065798 A1 | 3/2011 | Hoang et al. |
| 2011/0150958 A1 | 6/2011 | Davis et al. |
| 2011/0160663 A1 | 6/2011 | Stout et al. |
| 2011/0218529 A1 | 9/2011 | Garcia et al. |
| 2011/0319825 A1 | 12/2011 | Goral et al. |

FOREIGN PATENT DOCUMENTS

| | | |
|---|---|---|
| CN | 101353545 A | 1/2009 |
| CN | 102070983 A | 5/2011 |
| DE | 4011867 A1 | 10/1991 |
| EP | 0 036 294 A2 | 9/1981 |
| EP | 0 338 418 A1 | 10/1989 |
| EP | 0 379 271 A2 | 7/1990 |
| EP | 0 414 997 A1 | 3/1991 |
| JP | 05-277434 | 10/1993 |
| JP | 07-051651 | 2/1995 |
| JP | 08-209064 | 8/1996 |
| JP | 8-311373 A | 11/1996 |
| JP | 09-151262 | 6/1997 |
| JP | 09-157548 | 6/1997 |
| JP | 2000-178475 A | 6/2000 |
| JP | 2000-264803 A | 9/2000 |
| JP | 2001-072438 A | 3/2001 |
| JP | 2002-282762 | 10/2002 |
| JP | 2003-342402 | 12/2003 |
| JP | 2004-043669 A | 2/2004 |
| JP | 2005-028209 A | 2/2005 |
| JP | 2005-520912 A | 7/2005 |
| JP | 2007-016096 A | 1/2007 |

(56) References Cited

FOREIGN PATENT DOCUMENTS

| | | | |
|---|---|---|---|
| KR | 20020066429 A1 | 8/2002 |
| WO | 98/58690 | 12/1998 |
| WO | 98/58989 | 12/1998 |
| WO | 99/32168 | 7/1999 |
| WO | 00/66189 | 11/2000 |
| WO | 2006/056482 A1 | 6/2006 |
| WO | 2006/074666 A2 | 7/2006 |
| WO | 2006/088288 A1 | 8/2006 |
| WO | 2006/099358 A2 | 9/2006 |
| WO | 2007/095576 A2 | 8/2007 |
| WO | 2007/100653 A2 | 9/2007 |
| WO | 2007/100776 A2 | 9/2007 |
| WO | 2008/014438 A2 | 1/2008 |
| WO | 2008014447 A2 | 1/2008 |
| WO | 2008/031601 A1 | 3/2008 |
| WO | 2008/045761 A2 | 4/2008 |
| WO | 2008/128896 A2 | 10/2008 |
| WO | 2008/132045 A2 | 11/2008 |
| WO | 2009/070227 A1 | 6/2009 |

OTHER PUBLICATIONS

"Lubricent—Lubricious Hydrophillic Coatings for Medical Devices," Harland Medical Systems, http://www.harlandmedical.com/index.php/materials/lubricent.html, pp. 1-2, Printed Apr. 22, 2013.

"UV & EB Cure," Xiper Innovations, Inc., http://xiperinnovations.com/uv_eb_cure, Printed Apr. 22, 2013.

Cabot Corporation, "Using Silicas and Aluminas in Coatings,", www.cabot-corp.com/Silicas-And-Aluminas/Coatings, downloaded from the internet on Apr. 26, 2011.

McDonnell, G., Russell, A.D. Antiseptics and Disinfectants: Activity, Action, and Resistance. Clinical Microbiology Reviews, (1999) 12(1), pp. 149-179.

* cited by examiner

BLOOD CONTROL IV CATHETER WITH ANTIMICROBIAL PROPERTIES

BACKGROUND OF THE INVENTION

The current invention relates to systems and methods for coating various surfaces of medical devices with an anti-pathogenic material. In particular, the present invention relates to systems and methods for identifying surfaces within a medical device which include noncritical dimensions, wherein an anti-pathogenic material is applied to these identified surfaces to reduce or eliminate pathogenic colonization and growth within the medical device.

A formidable challenge of modern medical treatment is control of infection in the spread of pathogenic organisms. One area where this challenge is constantly presented is in infusion therapy of various types. Infusion therapy is one of the most common healthcare procedures. Hospitalized, home care, and other patients receive fluids, pharmaceuticals, and blood products via a vascular access device inserted into the vascular system of the patient. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access the patient's peripheral or central vasculature. The vascular access device may be indwelling for short-term (days), moderate term (weeks), or long-term (months two years). The vascular access device may be used for continuous infusion therapy or for intermittent therapy.

A common vascular access device comprises a plastic catheter inserted into a patient's vein. The catheter length may vary from a few centimeters or peripheral access, to many centimeters for central access and may include devices such as peripherally inserted central catheters (PICC). The catheter may be inserted transcutaneously or may be surgically implanted beneath the patient's skin. The catheter, or any other vascular access device attached thereto, may have a single lumen or multiple lumens for infusion of many fluids simultaneously.

A vascular access device may serve as a nidus, resulting in a disseminated BSI (blood stream infection). This may be caused by failure to regularly flush the device, a non-sterile insertion technique, or by pathogens that enter the fluid flow path through either end of the path subsequent to catheter insertion. When a vascular access device is contaminated, pathogens adhere to the vascular access device, colonize, and form a biofilm. The biofilm is resistant to most biocidal agents and provides a replenishing source of pathogens to enter a patient's bloodstream and cause a BSI.

One approach to preventing biofilm formation and patient infection is to provide an anti-pathogenic coating on various medical devices and components. However, some medical devices and components comprise materials or features which are incompatible with anti-pathogenic coatings. Thus, although methods exist for providing an anti-pathogenic coating on various medical devices and components, challenges still exist. Accordingly, it would be an improvement in the art to augment or even replace current techniques with other techniques. Such techniques are disclosed herein.

BRIEF SUMMARY OF THE INVENTION

In order to overcome the limitations discussed above, the present invention relates to systems and methods for selectively coating non-dimensionally critical surfaces of medical devices which contact blood or other fluids as part of an infusion therapy.

Some implementations of the present invention include an infusion therapy medical device having a surface which includes a noncritical dimension, wherein an anti-pathogenic material is applied to the surface. In some instances, the surface further comprises a portion of a fluid pathway through the device. Thus, the anti-pathogenic material is exposed to a fluid flowing through the fluid pathway of the device.

In some instances, an infusion therapy medical device is provided having a septum actuator which includes a probe portion configured to advance through a septum of the device upon actuation of the septum actuator. In some implementations, an anti-pathogenic material including a lubricant agent is applied to the probe portion of the septum actuator to reduce friction between the septum actuator and the septum during activation of the device. In other implementations, a rigid or semirigid anti-pathogenic material is applied to various surfaces of a base portion of the septum actuator.

Certain aspects of the present invention further include a color code system, whereby the identity of the anti-pathogenic material is identified based upon the color of the medical device.

Some aspects of the present invention include a medical device having a compatible surface which includes at least one mechanical bond whereby to facilitate binding between the surface and an anti-pathogenic material. Other aspects of the invention include providing a chemical bond between a compatible surface of a medical device and an anti-pathogenic material by surface cross-linking.

The present invention further includes various methods, techniques, and materials for identifying and coating surfaces of medical devices which include noncritical dimensions. Thus, an anti-pathogenic material may be applied to various surfaces within a medical device to reduce or eliminate pathogenic colonization and/or growth within the medical device thereby reducing the risk of pathogenic infection in patients.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

Figure 1:
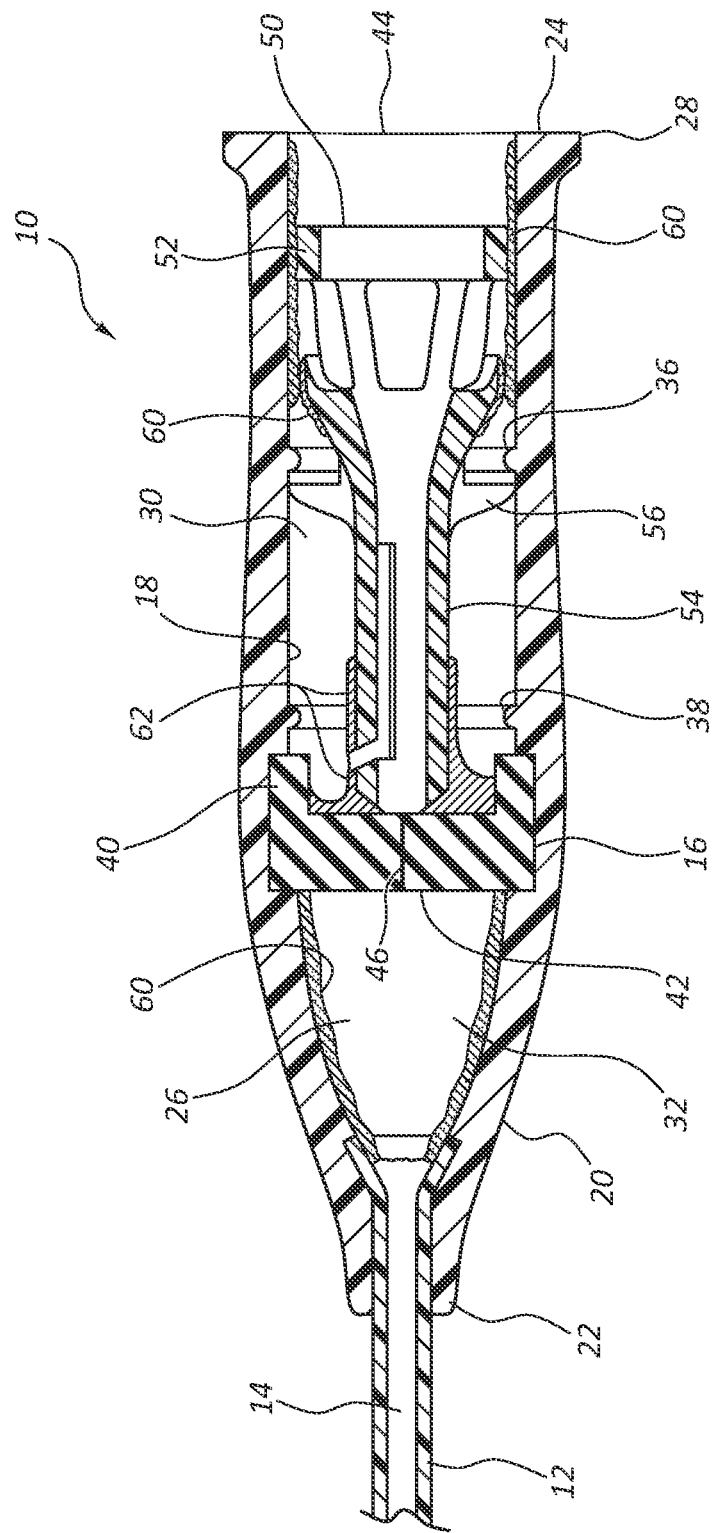
FIG. 1 is a cross-section view of a catheter assembly comprising a septum actuator prior to activation, the catheter assembly and septum actuator having various surfaces with critical and noncritical dimensions in accordance with a representative embodiment of the present invention.

The presently preferred embodiment of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The term "proximal" is used to denote a portion of a device which, during normal use, is nearest the user and furthest from the patient. The term "distal" is used to denote a portion of a device which, during normal use, is farthest away from the user wielding the device and closest to the patient. The term "activation" of valve mechanism or septum is used to denote the action of opening or closing of such valve. For example, in some embodiments a catheter assembly is provided having a septum and a septum actuator, wherein the catheter assembly undergoes activation when the septum actuator is advanced through the septum, thereby providing a fluid pathway through the septum.

The term "critical dimension" is used to denote at least one of a height, a length, a width, a depth, a diameter, a thickness, an angle, a texture, or other structural feature of a surface of a medical device which is critical to the operation of the device. For example, in some embodiments a medical device may include a surface that is configured to interface with another device or component. As such, the surface may include a critical dimension that is configured to accommodate optimal interaction between the surface of the medical device and the interfacing device or component. Thus, in some embodiments a surface having a critical dimension must remain unmodified to preserve the intended and/or desired interaction of the surface in operating or using the medical device. Conversely, the term "noncritical dimension" is used to denote at least one of a height, a length, a width, a depth, a diameter, a thickness, an angle, a texture, or other structural feature of a medical device with is not critical to the operation of the device.

The terms "chemical bond" or "chemical bonding" are used to denote an attraction between atoms that allows an anti-pathogenic material to be applied to a desired surface of a medical device. For example, in some instances an anti-pathogenic material of the present invention is applied to the surface of an infusion therapy medical device via chemical bonding, wherein atoms of the anti-pathogenic material and atoms of the medical device are chemically attracted to one another. Chemical bonding may include any type of atomic bond, such as a covalent bond, an ionic bond, dipole-dipole interactions, London dispersion force, Van der Waals force, and hydrogen bonding. A chemical bond may further be denoted by the terms "cross-linking" or "surface cross-linking" for some embodiments.

The terms "mechanical bond" or "mechanical bonding" are used to denote a physical, non-chemical interaction between two or more materials. For example, in some instances a surface of a medical device is altered to include a texture, a groove and/or a ridge having a void which holds an anti-pathogenic material via capillary force. In other embodiments, a mechanical bond comprises a structural feature which provides increased surface area to a surface of a medical device. Further, in some embodiments a mechanical bond comprises a hydrophilic or hydrophobic material or coating that is applied to a surface of a medical device to attract an anti-pathogenic material. A mechanical bond may further be denoted by the term "mechanical interlock" for some embodiments.

The term "compatible surface" is used to denote a surface of a medical device which includes a noncritical dimension, or a surface which includes a critical dimension that will not be adversely affected by the addition of an anti-pathogenic material or coating.

The terms "rigid" or "semirigid" are used to denote a physical property of an anti-pathogenic material, wherein the material is deficient in, or devoid, or mostly devoid of flexibility. Alternatively, these terms are used to denote an inflexible or mostly inflexible physical property of an anti-pathogenic material when applied or coated onto a surface of a device. In some instances, the term semirigid is understood to describe a physical property of an anti-pathogenic material that is rigid to some degree or in some parts.

The term "modified rheology" is used to denote a physical property of an anti-pathogenic material, wherein the viscosity of an anti-pathogenic material is modified to prevent excessive migration of the anti-pathogenic material once applied to a surface of a device. As such, the modified rheology of the anti-pathogenic material prevents or substantially prevents contact between the anti-pathogenic material and adjacent surfaces or components.

The term "anti-pathogenic" is used to denote a material, such as a coating material, that acts against pathogens. Pathogens may include any organism or substance capable of causing a disease, such as bacteria, viruses, protozoa and fungi. Accordingly, an "anti-pathogenic material" as contemplated herein includes any material having properties for acting against a pathogen.

The present invention relates generally to systems and methods for applying anti-pathogenic materials to various surfaces of medical devices. In particular, the present invention relates to systems and methods for applying anti-pathogenic materials to surfaces of medical devices for infusion therapies, wherein the surface comprises a portion of a fluid pathway of the medical device. In some instances, an anti-pathogenic material is applied to a surface comprising a noncritical dimension. In some embodiments, an anti-pathogenic material is applied to one or more surfaces of a medical device prior to assembling the medical device. In other embodiments, an anti-pathogenic material is applied to first portion or component of a medical device and subsequently transferred to a second portion or component of the medical device through controlled migration of the anti-pathogenic material. In other instances, an anti-pathogenic material is intermixed with, or incorporated into the material of the medical device during a molding process of the device. Further, in some instances an anti-pathogenic material is applied to or incorporated into the material of a medical device such that the anti-pathogenic material elutes out from the material of the medical device into the immediate surroundings of the coated medical device.

In general, an anti-pathogenic material in accordance with the present invention may include any material having anti-pathogenic properties which may be applied to the surface of a medical device. For example, in some embodiments an anti-pathogenic material may include an antimicrobial composition, as taught in U.S. patent application Ser. Nos. 12/397,760, 11/829,010, 12/476,997, 12/490,235, and 12/831,880, each of which is incorporated herein by reference, in its entirety. In some embodiments, an anti-pathogenic material may further include an anti-infective or antimicrobial lubricant, as taught in U.S. patent application Ser. Nos. 12/436,404 and 12/561,863, each of which is incorporated herein in its entirety. Further, in some embodiments an anti-pathogenic material is incorporated into the material of a medical device, or a component thereof, such as a septum actuator.

Some embodiments of the present invention comprise a medical device or component having at least one surface that defines a portion of a fluid pathway through the medical device. The surface of the medical device is coated with an anti-pathogenic material to prevent colonization of pathogens on the coated surface.

The application of an anti-pathogenic material to the surface of a medical device results in the addition of a layer or "coat" of anti-pathogenic material to the surface. This layer of anti-pathogenic material has a dimension (i.e. thickness) which may affect a relationship between the coated surface and an interfacing or adjacent component of the medical device. For example, in some embodiments a medical device may include an aperture having a diameter to compatibly receive a second medical device, such as by a friction, press, mechanical or interference fit. As such, the diameter of the aperture includes critical dimensions to ensure proper fitting between the aperture and the second medical device. In this example, the addition of an anti-pathogenic material to the surface of the aperture will adjust the diameter of the aperture thereby adversely affecting the ability of the aperture to receive the second medical device.

Accordingly, in some embodiments of the present invention it is undesirable to modify or coat a surface of a medical device or component wherein the surface includes a critical dimension that will be adversely affected by the addition of the anti-pathogenic material. Thus, some embodiments of the present invention comprise a method for coating a medical device with an anti-pathogenic material, wherein the method includes a first step of identifying surfaces of the medical device which include noncritical dimensions. The method may further include a step whereby the surfaces having noncritical dimensions are then coated with an anti-pathogenic material. Some methods of the present invention may further include steps for identify and isolating surfaces of the medical device having critical dimensions, prior to coating the remaining surfaces with an anti-pathogenic material.

In further example of the teachings of the present invention, a catheter assembly device 10 is shown in FIGS. 1-4. Catheter assembly device 10 provides a non-limiting example of a medical device having various surfaces which may be coated with an anti-pathogenic material. Accordingly, catheter assembly device 10 provides a representative embodiment on which to demonstrate and discuss the methodologies of the present invention relating to the selection and coating of surfaces with an anti-pathogenic material.

Referring now to FIG. 1, a cross-section view of a catheter assembly 10 is shown. Catheter assembly 10 generally includes a catheter 12 coupled to a distal end 22 of a catheter adapter 20. Catheter 12 and catheter adapter 20 are integrally coupled such that can internal lumen 26 of catheter adapter 20 is in fluid communication with a lumen 14 of catheter 12. Catheter 12 generally comprises a biocompatible material having sufficient rigidity twisting pressures associated with insertion of the catheter into a patient. In some embodiments, catheter 12 comprises a metallic material, such as titanium, stainless steel, nickel, molybdenum, surgical steel, and alloys thereof. In other embodiments, catheter 12 comprises a rigid, polymer material, such as vinyl or silicon.

Catheter assembly 10 may further include features for use with an over-the-needle catheter assembly. For example, a flexible or semi flexible polymer catheter may be used in combination with a rigid introducer needle to enable insertion of the catheter into the vasculature of a patient. Surgically implanted catheters may also be used.

Once inserted into a patient, catheter 12 and catheter adapter 14 provide a fluid conduit to facilitate delivery of a fluid to and/or retrieval of a fluid from a patient, as required by a desired infusion procedure. Thus, in some embodiments the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing (not shown) to further facilitate delivery of a fluid to or removal of a fluid from a patient.

The various embodiments of the present invention may be adapted for use with any medical device or accessory having a lumen in which is seated a septum. For example, in some embodiments a female Luer adapter coupled to a section of intravenous tubing may comprise a septum and a septum actuator in accordance with the present teachings. In other embodiments, one or more ends of a y-port adapter may comprise a septum and a septum actuator in accordance with the teachings of the present invention.

In some embodiments, a proximal end 24 of the catheter adapter 14 includes a flange 28. Flange 28 provides a positive surface which may be configured to enable coupling of intravenous tubing or a Luer adapter to the catheter assembly 10. In some embodiments, flange 28 further includes a set of threads to accept a Luer adapter via a threaded connection.

In some embodiments, an inner surface of catheter adapter 20 comprises a groove or channel 16 in which is seated a septum 40. Septum 40 generally comprises a flexible, or semi-flexible polymer plug having an outer diameter that is configured to compatibly seat within channel 16. In some embodiments, septum 40 is barrel shaped having a barrier surface 42 comprising a distal end of the septum 40 and further having an opening 44 comprising a proximal end of the septum 40. When positioned within channel 16, barrier surface 42 divides inner lumen 26 into a proximal fluid chamber 30 and a distal fluid chamber 32. Thus, the presence of septum 40 controls or limits passage of fluid between the proximal and distal fluid chambers 30 and 32.

In some embodiments, catheter assembly 10 further comprises a septum actuator 50. Septum actuator 50 is generally positioned within proximal fluid chamber 30 at a position adjacent septum 40. In some instances, septum actuator 50 comprises a base 52 which is positioned adjacent to a proximal opening 44 of catheter adapter 20. Septum actuator 50 further comprises a probe 54 which is positioned adjacent barrier surface 42 of septum 40 prior to activation of catheter assembly 10.

In some embodiments, septum actuator 50 is slidably housed within catheter adapter 20, such that septum actuator 50 comprises an independent component of catheter assembly 10. Septum actuator 50 may be coated with an anti-pathogenic material prior to being inserted into catheter adapter 20. In some instances, septum actuator 50 is coated with a rigid or semirigid anti-pathogenic material such that fluid which bypasses septum actuator 50 comes in contact with the anti-pathogenic material. In other instances, septum actuator 50 is coated with a viscous or fluid anti-pathogenic material such that the anti-pathogenic material is transferred to surfaces of catheter assembly 10 which come in contact with the anti-pathogenic material. Further still, in some instances the material of septum actuator 50 comprises an anti-pathogenic material or agent. For example, the material of septum actuator 50 may include an anti-pathogenic material which is incorporated into or admixed with the material of septum actuator 50 during a molding process. In some instances, the anti-pathogenic material is capable of eluding out of septum actuator 50 into the surrounding areas within the catheter adapter 20. For example, a fluid passing through catheter adapter 20 may be treated with the anti-pathogenic material of septum actuator 50 by either directly contacting the anti-pathogenic material or by contacting anti-pathogenic material which has eluded from the material of septum actuator 50.

In some embodiments, a septum actuator 50 is provided within a fluid pathway of catheter assembly 10, such that all fluid passing through catheter assembly 10 come in contact with septum actuator 50, or pass in proximity to septum actuator 50 through immediate surroundings of septum actuator 50. Thus, some embodiments of the present invention provide anti-pathogenic treatment of a fluid within catheter assembly 10 by providing a septum actuator 50 having an external or exposed surface which is coated with anti-pathogenic material. Further, some embodiments of the present invention prevent bacterial colonization within a fluid pathway of catheter assembly 10 by providing a septum actuator 50 having an anti-pathogenic coating material coated thereon. In some instances, an anti-pathogenic material is applied to various surfaces of septum actuator 50 which comprise noncritical dimensions. In other instances, an anti-pathogenic material is applied to various surfaces of septum actuator 50 which comprise critical and noncritical dimensions. Further still, in some instances an anti-pathogenic material is applied to all surfaces of septum actuator 50 which may come in contact with a fluid flowing through a fluid pathway of catheter assembly 10.

Septum actuator 50 may comprises various features to facilitate use of septum actuator 50 within catheter assembly 10. For example, septum actuator 50 may include various vents and other structural features to control fluid flow through and around septum actuator 50, as taught in U.S. patent application Ser. Nos. 12/703,336 and 12/703,406, each of which is incorporated herein by reference, in its entirety. Septum actuator 50 may further include structural features to maintain the position of septum actuator 50 within lumen 26 of catheter adapter 20. For example, in some embodiments septum actuator 50 comprises fins 56 which are seated in channel 18 of catheter adapter 20. Channel 18 restricts proximal and distal movement of septum actuator 50 between proximal and distal stops 36 and 38, respectively. Accordingly, prior to activation fins 56 are positioned proximally within channel 18, adjacent proximal stop 36. Upon activation, septum actuator 50 is advanced distally within channel 18 until fins 56 contact distal stop 38.

As discussed previously, various surfaces of catheter assembly 10 comprise critical dimensions which may be adversely affected by the addition of an anti-pathogenic coating or material. For example, channel or groove 16 comprises an inner diameter having a critical dimension configured to receive septum 40. Accordingly, in some embodiments it is undesirable to apply an anti-pathogenic material to the surface of groove 16. Similarly, in some embodiments it is undesirable to apply an anti-pathogenic material to the outer surface of septum 40, wherein the diameter of the outer surface of septum 40 comprises a critical dimension configured to form an interface with groove 16.

Further, channel 18 comprises a width, depth and length configured to compatibly and slidably receive fins 56 of septum actuator 50. Accordingly, these dimensions of channel 18 comprise critical dimensions which may be undesirably affected by the addition of an anti-pathogenic material. Thus, in some embodiments it is undesirable to apply an anti-pathogenic material to the surfaces of channel 18. Similarly, in some embodiments it is undesirable to apply an anti-pathogenic material to the tips or interfacing surfaces of fins 56, wherein the tips or interfacing surfaces of fins 56 comprise a critical dimension configured to compatibly seat and slide within channel 18.

Catheter assembly 10 further comprises various surfaces which may be coated with an anti-pathogenic material, wherein the surfaces include noncritical dimensions. For example, in some embodiments the inner surface of the distal fluid chamber 32 comprises a noncritical dimension and is therefore coated with an anti-pathogenic material 60. Similarly, various surfaces of base 52 of septum actuator 50 comprise noncritical dimensions and are therefore coated with anti-pathogenic material 60. Certain surfaces of proximal fluid chamber 30 further include noncritical dimensions and may therefore be coated with anti-pathogenic material 60. In particular, surfaces positioned between proximal stop 36 and opening 44 of catheter adapter 20 comprise noncritical dimensions.

In general, anti-pathogenic material may be applied to any internal or external surface of a medical device, or a component of a medical device, wherein the surface comprises or is exposed to a fluid pathway through the medical device. The surface may further include a critical or non-critical dimension. Pathogens within a fluid passing through the medical device are thus prevented from colonizing within the medical device. In some embodiments, the thickness of the anti-pathogenic material is proportionate to a duration of effectiveness of the anti-pathogenic material on the coated surface. Thus, the duration of effectiveness of the coating may be increased by increasing the thickness of the anti-pathogenic material applied to the surface. The duration of effectiveness may further be modified through modifying the physical properties of the anti-pathogenic material to increase or decrease the rate at which the anti-pathogenic agents are capable of eluting out of the coating material.

In some embodiments, a rigid or semirigid anti-pathogenic material 60 is selected which is configured to permit long-term elution of the anti-pathogenic agents contained within the material 60. As such, it is desirable to provide the anti-pathogenic material to much of the fluid path surface area of catheter assembly 10. In other embodiments, a viscous, fluid anti-pathogenic material 62 is selected which further comprises a lubricant agent. For example, in some embodiments an anti-pathogenic material 62 is provided which further includes a silicon lubricant agent, such as MED-460 (manufactured by NuSil Technology, LLC). The inclusion of a lubricious agent reduces friction between interfacing components of catheter assembly 10. For example, anti-pathogenic material 62 is applied to the probe portion 54 of septum actuator 50, thereby reducing friction between septum actuator 50 and septum 40. In some embodiments, anti-pathogenic material 62 further provides a fluid-tight seal between septum 40 and the outer surface of probe 54. Further, in some embodiments anti-pathogenic material 62 provides a fluid-tight seal to slit 46 of septum 40 prior to activation or provides a fluid-tight seal to slit 46 following removal of probe 54 from septum 40.

Anti-pathogenic material 62 may be applied to portions of probe 54 prior to assembling catheter assembly 10. In some embodiments, anti-pathogenic material 62 is capable of flowing or migrating when brought into contact with other surfaces. Accordingly, in some embodiments excess anti-pathogenic material 62 from probe 54 is applied to septum 40 following assembly of catheter assembly 10, as shown. In other embodiments, anti-pathogenic material 62 comprises a modified rheology to prevent or control excessive migration of anti-pathogenic material 62 within catheter adapter 20. For example, anti-pathogenic material 62 may further include rheological modifiers to increase the viscosity of the material, such as silica, talc or clay.

The process for coating or applying the anti-pathogenic material to compatible surfaces of catheter assembly 10 may be accomplished by dipping the desired portions or components of the device in their respective coating material 60 and/or 62. Alternatively, anti-pathogenic materials may be sprayed onto the desired surfaces. In some embodiments, surfaces having critical dimensions are masked or otherwise protected prior to applying the anti-pathogenic material to the remaining surfaces. Compatible surfaces may further include a mechanical feature to encourage mechanical binding between the coating material and the compatible surface.

For example, a compatible surface may be designed to include a physical feature that increases mechanical binding of the coating material, such as a texture, a groove, a ridge or some other feature which increases the surface area of the compatible surface. In some embodiments, a mechanical bond is facilitated by a mechanical interlock comprising a void which holds the anti-pathogenic material by capillary force or surface tension forces. In other embodiments, a mechanical interlock comprises a hydrophilic or hydrophobic material or coating that is applied to the compatible surface to attract the anti-pathogenic material.

Further, in some embodiments the anti-pathogenic material is chemically bound to the compatible surface of the catheter assembly or medical device by a chemical bond, such as surface cross-linking. For example, in some embodiments a compatible surface of a device comprises a polymer material that is capable of forming chemical bonds with at least one component of an anti-pathogenic material. Non-limiting examples of polymer materials which may be used to achieve surface cross-linking include polycarbonate, polyester, and polyurethane. In some instances, an anti-pathogenic material is applied to a compatible surface of a device and then cured to achieve surface cross-linking between the anti-pathogenic material and the surface of the device.

Figure 2:
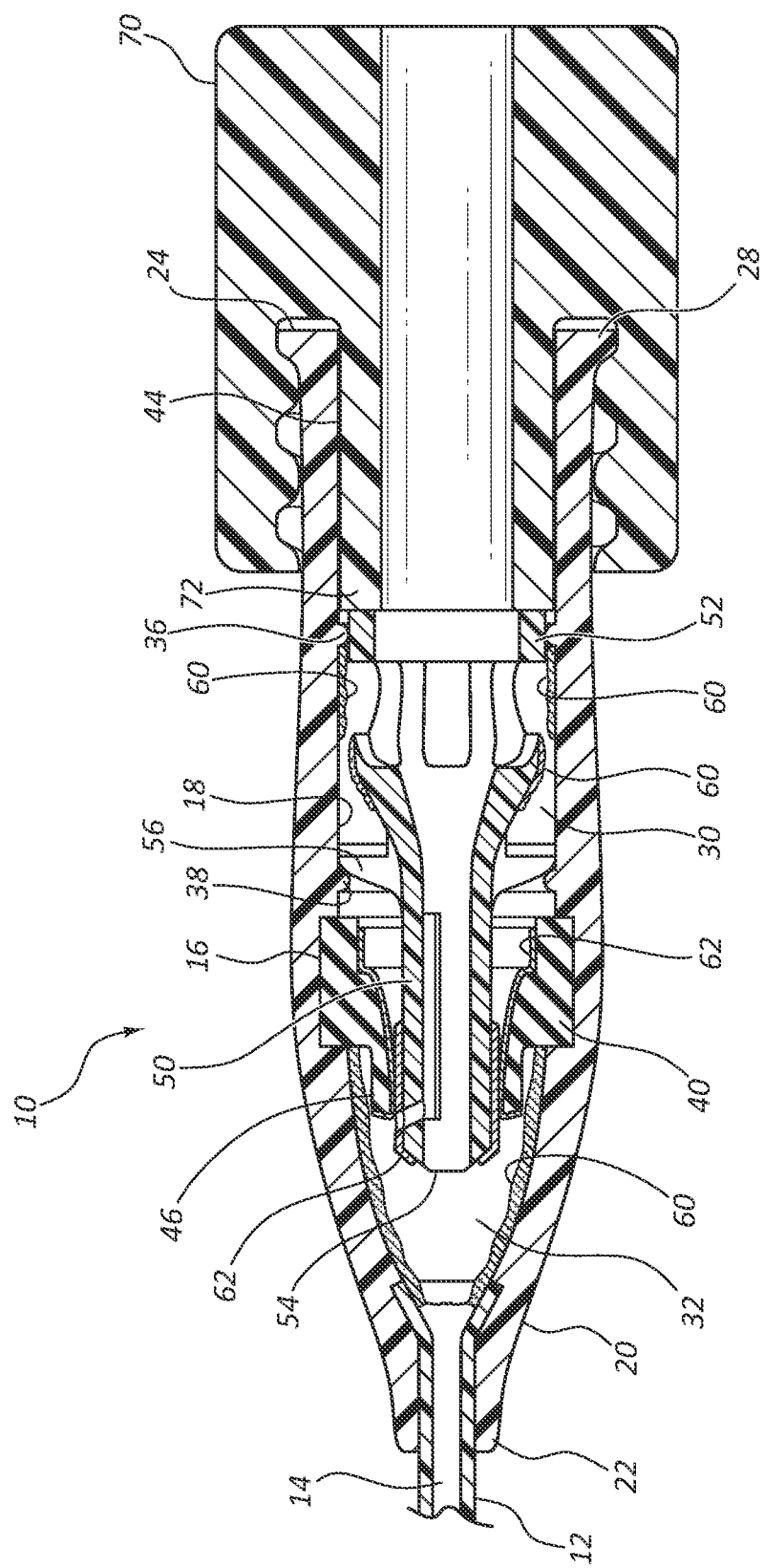
FIG. 2 is a cross-section view of the catheter assembly comprising a septum actuator following activation in accordance with a representative embodiment of the present invention.

Referring now to FIG. 2, catheter assembly 10 is shown following activation with a Luer adapter 70. Catheter assembly 10 is activated as septum actuator 50 is advanced distally thereby causing probe 54 to advance through slit 46 of septum 40. In some embodiments, septum actuator 50 is advanced distally as Luer adapter 70 is inserted into opening 44 of catheter adapter 20. In some embodiment, opening 44 comprises a diameter and inner wall surface angle that is configured to receive probe 72 of Luer adapter 70 in a friction or interference fit. Accordingly, in some embodiments it is undesirable to apply an anti-pathogenic material to opening 44, wherein an anti-pathogenic coating would adversely affect the fit of probe 72 within opening 44.

Alternatively, in some embodiments opening 44 may be coated with an anti-pathogenic material that is viscous, yet fluid enough to be displaced by probe 72 upon coupling of Luer adapter 70 to proximal end 24. In these embodiments, the anti-pathogenic material may act as sealant between probe 72 and opening 44, wherein probe 72 removes the necessary excess amount of anti-pathogenic material to leave a small amount of anti-pathogenic material between the interfacing surface of opening 44 and probe 72.

Figure 3:
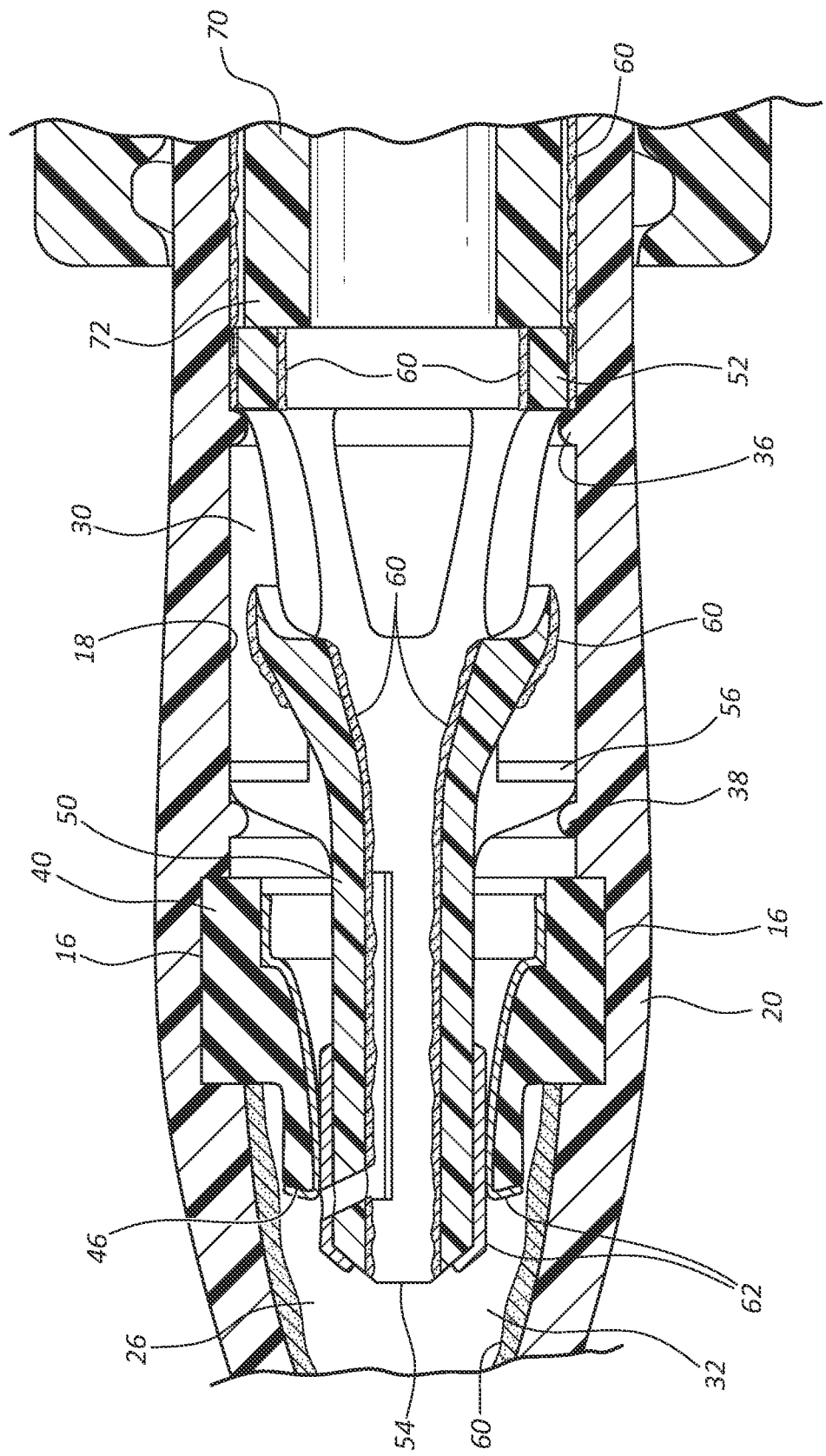
FIG. 3 is a detailed, cross-section view of a catheter assembly comprising a septum actuator following activation in accordance with a representative embodiment of the present invention.

In some embodiments, an anti-pathogenic material 62 is configured to transfer to interfacing surface within the catheter assembly 10 following activation. For example, in some embodiments anti-pathogenic material on probe 54 of septum actuator 50 is transferred to septum 50 and the septum slit 46 as probe 54 is advanced through slit 46. Further, anti-pathogenic material 60 on base 52 of septum actuator 50 is transferred to channel 18 as septum actuator 50 is advanced distally within catheter adapter 20. Thus, anti-pathogenic material 60 may be applied to various surfaces of catheter assembly 10 in anticipation of further distribution of the anti-pathogenic material following activation of the catheter assembly 10. In other embodiments, anti-pathogenic material 60 comprises a rigid or semirigid material that is not transferred during activation of catheter assembly 10. A detailed view of catheter assembly 10 following activation is shown in FIG. 3.

In some embodiments, various other structural features and/or surfaces of catheter assembly 10 may include critical dimensions on which it is undesirable to apply an anti-pathogenic material. For example, in some infusion therapy techniques it is desirable to permit a controlled flow of fluid through the septum 40 prior to activating the septum 40 with the septum activator 50. Thus, in some embodiments slit 46 may further comprise a leak orifice having an opening diameter calculated to permit controlled flow of liquid or air between the proximal and distal fluid chambers 30 and 32. As this leak orifice includes critical dimensions, it would be undesirable to block or reduce the calculated opening diameter by the addition of an anti-pathogenic material. Further, groove or channel 16 may be modified to include air channels to permit passage of air between proximal and distal fluid chambers 30 and 32. These too would include critical dimensions that would be adversely affected by the addition of an anti-pathogenic material.

Figure 4:
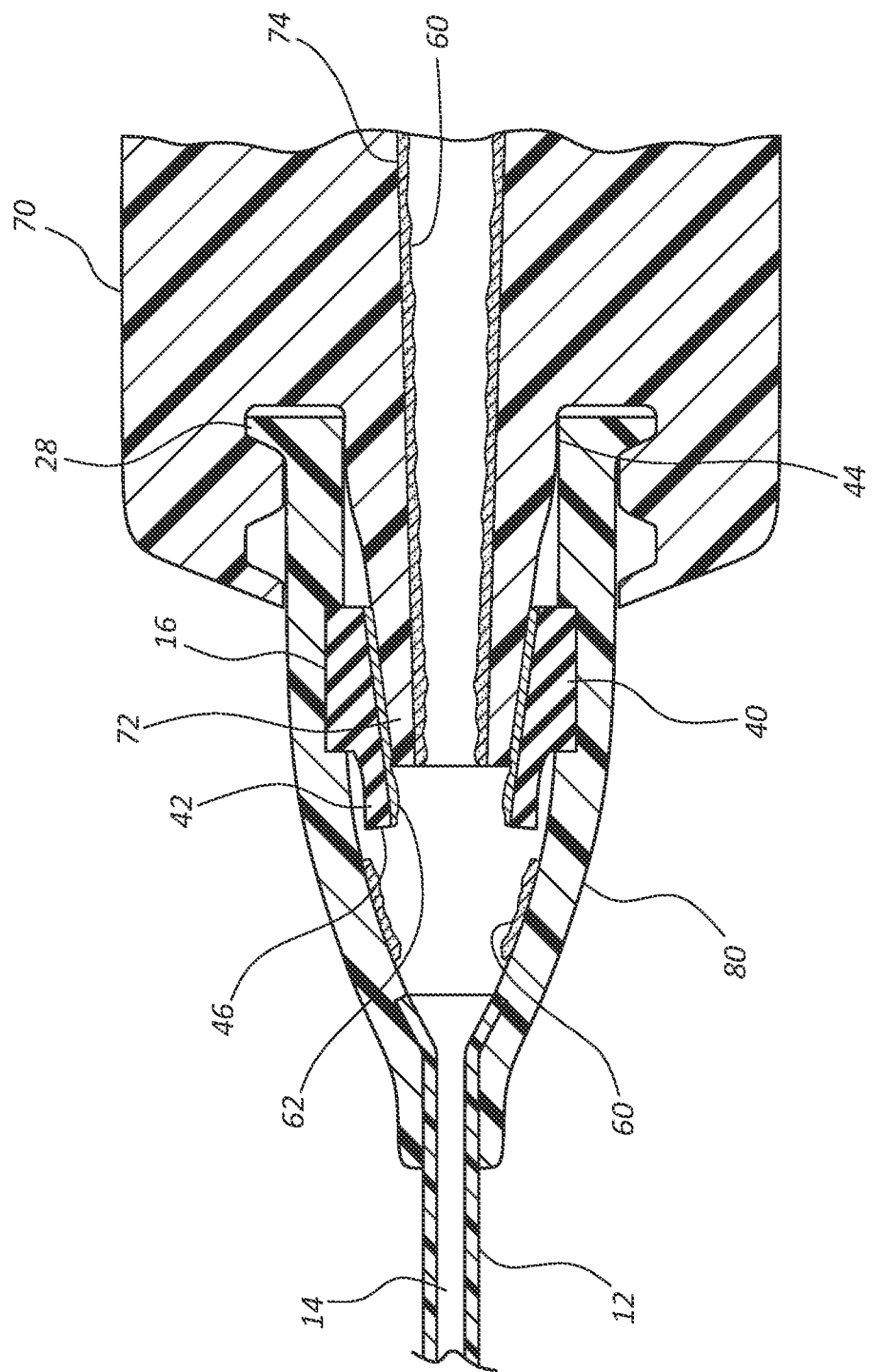
FIG. 4 is a cross-section view of a catheter assembly following activation via a Luer adapter in accordance with a representative embodiment of the present invention.

Referring now to FIG. 4, a catheter assembly 80 is shown following activation via a Luer adapter 70. In some embodiments, a catheter assembly 80 is provided which includes a septum 40 that is positioned proximate to opening 44, such that septum 40 may be actuated directly by a probe portion 72 of Luer adapter 70. As discussed previously, various surfaces of catheter assembly 80 are coated with an anti-pathogenic material 60 and/or 62. Surfaces and portions of catheter assembly and Luer adapter 70 which are determined to include critical dimensions are not coated with the anti-pathogenic material. However, in some embodiments an anti-pathogenic material 60 is applied to the fluid pathway 74 of Luer adapter 70, wherein it is determined that the dimensions of fluid pathway 74 comprise noncritical dimensions. Luer adapter 70 may further comprise a female Luer adapter, or a male Luer adapter.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An infusion therapy medical device, comprising:
   a catheter adapter from which a catheter extends distally, the catheter adapter including a lumen, the lumen including a channel formed between a proximal stop and a distal stop;
   a septum positioned within the lumen distal to the distal stop, the septum dividing the lumen into a distal fluid chamber and a proximal fluid chamber;
   an introducer needle that extends through the lumen of the catheter adapter and through the catheter to allow the catheter to be inserted into a patient's vasculature, the introducer needle being configured to be removed from the lumen after insertion of the catheter; and a septum actuator disposed within the proximal fluid chamber, the septum actuator comprising a body with a lumen and a plurality of fins that extend radially outward from the body, the septum actuator being configured to move from a proximal position in which the fins contact the proximal stop to a distal position in which the fins contact the distal stop, and wherein, when in the distal position, a distal end of the septum actuator extends through the septum, the septum actuator including a rigid or semi-rigid anti-pathogenic material that is applied to a portion of the body but that is not applied to tips of the fins.

2. The device of claim 1, wherein the portion of the body to which the rigid or semi-rigid anti-pathogenic material is applied comprises an external surface.

3. The device of claim 1, wherein the portion of the body to which the rigid or semi-rigid anti-pathogenic material is applied comprises an internal surface.

4. The device of claim 1, wherein the device is selected from the group consisting of a catheter adapter and a Luer adapter.

5. The device of claim 1, further comprising:
a viscous or fluid anti-pathogenic material applied to a portion of the body of the septum actuator.

6. The device of claim 1, further comprising:
a viscous or fluid anti-pathogenic material applied to a portion of the septum.

7. The device of claim 1, wherein the rigid or semi-rigid anti-pathogenic material is applied to a portion of the lumen of the infusion therapy medical device but not to the channel.

8. The device of claim 7, wherein the portion of the lumen of the infusion therapy medical device includes a portion distal to the septum.

9. The device of claim 1, further comprising an identifying color to indicate a specific type of the anti-pathogenic material.

10. The device of claim 1, wherein the rigid or semi-rigid anti-pathogenic material is applied to the portion of the body at a desired thickness that is proportionate to a duration of effectiveness of the anti-pathogenic material on the portion of the body.

* * * * *